United States Patent
Min et al.

(10) Patent No.: US 11,129,993 B2
(45) Date of Patent: Sep. 28, 2021

(54) IMPLANTABLE MEDICAL DEVICE UTILIZING POSTURE AND HEART SOUNDS AND METHOD OF USING SAME

(71) Applicant: PACESETTER, INC., Sylmar, CA (US)

(72) Inventors: Xiaoyi Min, Simi Valley, CA (US); Kyungmoo Ryu, Palmdale, CA (US); Thanh Tieu, Simi Valley, CA (US); Gene A. Bornzin, Simi Valley, CA (US); Stuart Rosenberg, Castaic, CA (US)

(73) Assignee: Pacesetter, Inc., Sylmar, CA (US)

( * ) Notice: Subject to any disclaimer, the term of this patent is extended or adjusted under 35 U.S.C. 154(b) by 479 days.

(21) Appl. No.: 16/100,009

(22) Filed: Aug. 9, 2018

(65) Prior Publication Data

US 2020/0046982 A1    Feb. 13, 2020

(51) Int. Cl.
*A61N 1/365* (2006.01)
*A61N 1/362* (2006.01)

(52) U.S. Cl.
CPC ..... *A61N 1/36542* (2013.01); *A61N 1/36535* (2013.01); *A61N 1/3622* (2013.01)

(58) Field of Classification Search
CPC combination set(s) only.
See application file for complete search history.

(56) References Cited

U.S. PATENT DOCUMENTS 6,466,821 B1   10/2002   Pianca et al.
6,937,900 B1   8/2005   Pianca et al.
7,559,901 B2   7/2009   Maile et al.
2006/0161070 A1*   7/2006   Siejko ............... A61B 5/1107
                                                    600/528
2018/0185660 A1*   7/2018   Eddy .................. A61B 5/0464

OTHER PUBLICATIONS

Communication pursuant to Rules 161(1) and 162 EPC for corresponding EP. Application No. 19765575.6-1122 dated Mar. 16, 2021 (3 pages).
International Preliminary Report on Patentability for PCT Application No. PCT/US2019/045700 dated Feb. 9, 2021 (8 pages).

* cited by examiner

*Primary Examiner* — Scott Luan
(74) *Attorney, Agent, or Firm* — The Small Patent Law Group LLC; Dean D. Small

(57) ABSTRACT

A computer implemented method and system for detecting arrhythmias in cardiac activity are provided. The method is under control of one or more processors configured with specific executable instructions. The method obtains cardiac activity (CA) signals at the electrodes of an implantable medical device (IMD) in connection multiple cardiac beats and with different IMD orientations relative to gravitational force. The method obtains acceleration signatures at a sensor of the IMD that are indicative of heart sounds generated during the cardiac beats. The method obtains device location information at the IMD, with respect to the gravitational force during the cardiac beats. The method groups the acceleration signatures associated with the first and second set of cardiac beats into the corresponding one of first and second posture bins based on the device location information. The method identifies a difference between the acceleration signals in the first posture bin in connection with treating a heart condition.

20 Claims, 11 Drawing Sheets

IMPLANTABLE MEDICAL DEVICE UTILIZING POSTURE AND HEART SOUNDS AND METHOD OF USING SAME

FIELD OF THE INVENTION

Embodiments herein generally relate to an implantable medical device (IMD), and more particularly to an IMD that utilizes posture and heart sounds in connection with arrhythmia detection.

BACKGROUND OF THE INVENTION

Various types of implantable medical devices (IMDs) are utilized today, including IMDs that deliver therapy and IMDs that merely monitor a patient. IMDs that do not delivery therapy are also referred to as an implantable cardiac monitor (ICM). An ICM is a small medical device placed beneath your chest muscle to continuously monitor cardiac activity and record electrocardiograms (ECGs) automatically. An ICM includes one or more combinations of electrodes to sense and record the cardiac activity. As the ICM records cardiac activity continuously and/or periodically, the patient will move between various states and postures.

ICMs are often utilized to help clinicians diagnose and treat abnormal heart activities that may be the cause of symptoms such as seizures, recurrent palpitations (e.g., noticeably rapid, strong, or irregular heartbeats due to agitation, exertion, or illness), lightheadedness, dizziness, or more importantly syncope (fainting). The abnormal heart activities include bradycardia arrhythmia (e.g., slow heart rate), tachycardia (e.g., fast heart rate), asystole (e.g., no electrical heart activity), atrial or ventricular arrhythmias (e.g., problems with rate or rhythm of heartbeat), and even atrial fibrillation (e.g., atrial fibrillation (AF), very fast or irregular heartbeat). The cardiac activity signals (e.g., EGM signals) may be analyzed by various arrhythmia detection algorithms. The same or different arrhythmia detection algorithms may be used by IMDs that delivery therapy and ICMs.

However, arrhythmia detection algorithms that analyze cardiac activity signals recorded by ICMs (and more generally all IMDs) may incorrectly interpret the cardiac activity signals and declare a false arrhythmia and/or fail to declare an arrhythmia. A desire remains to improve the reliability of arrhythmia detection algorithms and to reduce the number of false positive arrhythmia declarations. The reliability of the arrhythmia detection algorithms are dependent in part on the nature and quality of the cardiac activity signals recorded. The nature and quality of the recorded cardiac activity signals is dependent on various factors, including a position and orientation of the ICM and/or IMD. The ICM includes electrodes physically mounted within the housing of the ICM, and thus when the ICM housing shifts in position and/or orientation, the electrodes similarly shift. Some IMDs that delivery therapy also include electrodes physically mounted within the housing (e.g., leadless IMDs), and thus when the IMD housing shifts in position and/or orientation, the electrodes similarly shift.

The 3-D accelerometer may detect rotation based on the position and/or orientation of the ICM and more generally the IMD. For example, the 3-D accelerometer may detect a difference in the position and/or orientation of the IMD, based on the heart sound difference, which may be used in conjunction to determine a change in position of the IMD. Due to the linear shape and small size of an IMD, the device may rotate or otherwise move within a subcutaneous implant region. IMD rotation, translation, and motion may cause the device to inappropriately detect heart signals by altering the R-wave amplitudes and morphologies. Also, changes in the position and orientation of the IMD, and sensing electrodes, may alter the morphology of the recorded cardiac activity signals, including, among other things, the amplitude of the P waves, R waves, T waves and the like.

Further, the IMD includes a three-dimensional (3-D) accelerometer that is used to record posture and patient activity information. The 3-D accelerometers are calibrated with respect to a gravitational force of the earth, thereby defining the coordinate system of the IMD relative to gravity. When an IMD rotates, translates or otherwise moved within a subcutaneous implant region, the ICM undertakes a different position and orientation with respect to the patient, thereby causing a potential for in accuracy in posture detection and arrhythmia detection (when posture is utilized as a factor in the arrhythmia detection algorithm).

SUMMARY

A computer implemented method for detecting arrhythmias in cardiac activity is provided. The method is under control of one or more processors that are configured with specific executable instructions. The method obtains cardiac activity (CA) signals at the electrodes of an implantable medical device (IMD) in connection multiple cardiac beats and in connection with different IMD orientations relative to gravitational force. The method obtains acceleration signatures at a sensor of the IMD, that are indicative of heart sounds generated during the cardiac beats. The method obtains device location information at the IMD, with respect to the gravitational force during the cardiac beats. The method groups the acceleration signatures associated with the first and second set of cardiac beats into the corresponding one of first and second posture bins based on the device location information. The method identifies a difference between the acceleration signals in the first posture bin in connection with treating a heart condition.

Optionally, the method may include identifying differences or similarities between the acceleration signals and the second posture bin in connection with treating the heart condition. Additionally or alternatively, the method may include treating the heart condition by identifying a progression of heart failure over time, by confirming an arrhythmia identified by an arrhythmia detection process, or by constructing the patient to perform a recalibration procedure. Optionally, the method may include detecting an arrhythmia. The method may determine whether a current patient posture has changed based on the device location information. The method may include applying a new parameter value to an arrhythmia detection algorithm where the new parameter value may be based on the current patient posture.

Optionally, the method may include comparing a position that may not fall into the posture bins. The method may declare that the IMD drift condition has moved or rotated. Additionally or alternatively, the method may include determining a morphology characteristic of interest associated with the first posture first from one another by more than a correlation limit. When the correlation limit is exceeded, the declaration operation may comprise setting an IMD drift flag back to an ON condition. Additionally or alternatively, the first and second posture bins may correspond to first and second body postures, respectively. The determining operation may compare acceleration signatures in the first posture bin to one another and may compare the acceleration signatures in the second posture bin to one another to identify a progression of heart failure over time.

Optionally, the determining operation may avoid comparing acceleration signatures from a first posture bin with acceleration signatures from a second posture bin. The grouping operation may comprise grouping a first set of acceleration signatures. The method may group and store the acceleration signatures in the first and second posture bins for corresponding body postures and for corresponding heart rate ranges. The determining of the heart condition may be based, in part, on changes in heart sounds within the acceleration signatures for a first body posture and a first heart rate range. The difference may correspond to a difference in at least one of an S1 amplitude, an S1 frequency, or a peak to peak timing between heart sounds in the acceleration signatures. The method may assign the cardiac beats associated with the first posture to the first posture bin, and may assign the cardiac beats associated with the second posture to the second posture bin.

In accordance with embodiments herein, a system is provided. The system includes one or more processors and a memory coupled to the one or more processors. The memory stores program instructions. The program instructions are executable by the one or more processors. The system obtains cardiac activity (CA) signals, at electrodes of an implantable medical device (IMD), in connection multiple cardiac beats and in connection with different IMD orientations relative to gravitational force. The system obtains acceleration signatures at a sensor of the IMD indicative of heart sounds generated during the cardiac beats. The system obtains device location information at the IMD with respect to the gravitational force during the cardiac beats. The system groups the acceleration signatures associated with the first and second sets of cardiac beats and to a corresponding one of first and second posture bins based on the device location information. The system identifies a difference between the acceleration signal in the first posture bin in connection with treating a heart condition.

Optionally, the system may include one or more processors that may be configured to treat the heart condition by identifying a progression of heart failure over time, by confirming and an arrhythmia identified by an arrhythmia detection process, or by constructing the patient to perform a recalibration procedure. The one or more processors may be further configured to set an arrhythmia. The processors may determine whether a current patient posture has changed based on the device location information. The processors may apply a new parameter value to an arrhythmia detection algorithm. The new parameter value may be based on the current patient posture. The one or more processors may be configured to compare morphology characteristics of interest for acceleration signatures within the first posture bin to a correlation limit. Based on the comparing operation, the one or more processors may declare an IMD drift condition.

Optionally, the system may include a remote server or a local external device housing. They system may include at least one of the one or more processors that may be configured to determine the group and identify operations. The system may include a user interface. The one or more processors may be configured to implement a calibration procedure. The calibration procedure may provide a patient instruction through the user interface to move to a predefined posture and may collect device location information while at the predefined posture. The calibration procedure may calculate reference orientation angles and may store the reference posture data set. The reference posture data set may comprise the device location information and reference orientation angles. One or more processors may be configured to group and store the acceleration signatures into the first and second posture bins for corresponding body postures and for corresponding heart rate ranges. The one or more processors may be configured to determine the heart condition based in part on changes in heart sounds within the acceleration signatures for a first body posture and a first heart rate range.

DETAILED DESCRIPTION

Figure 1:
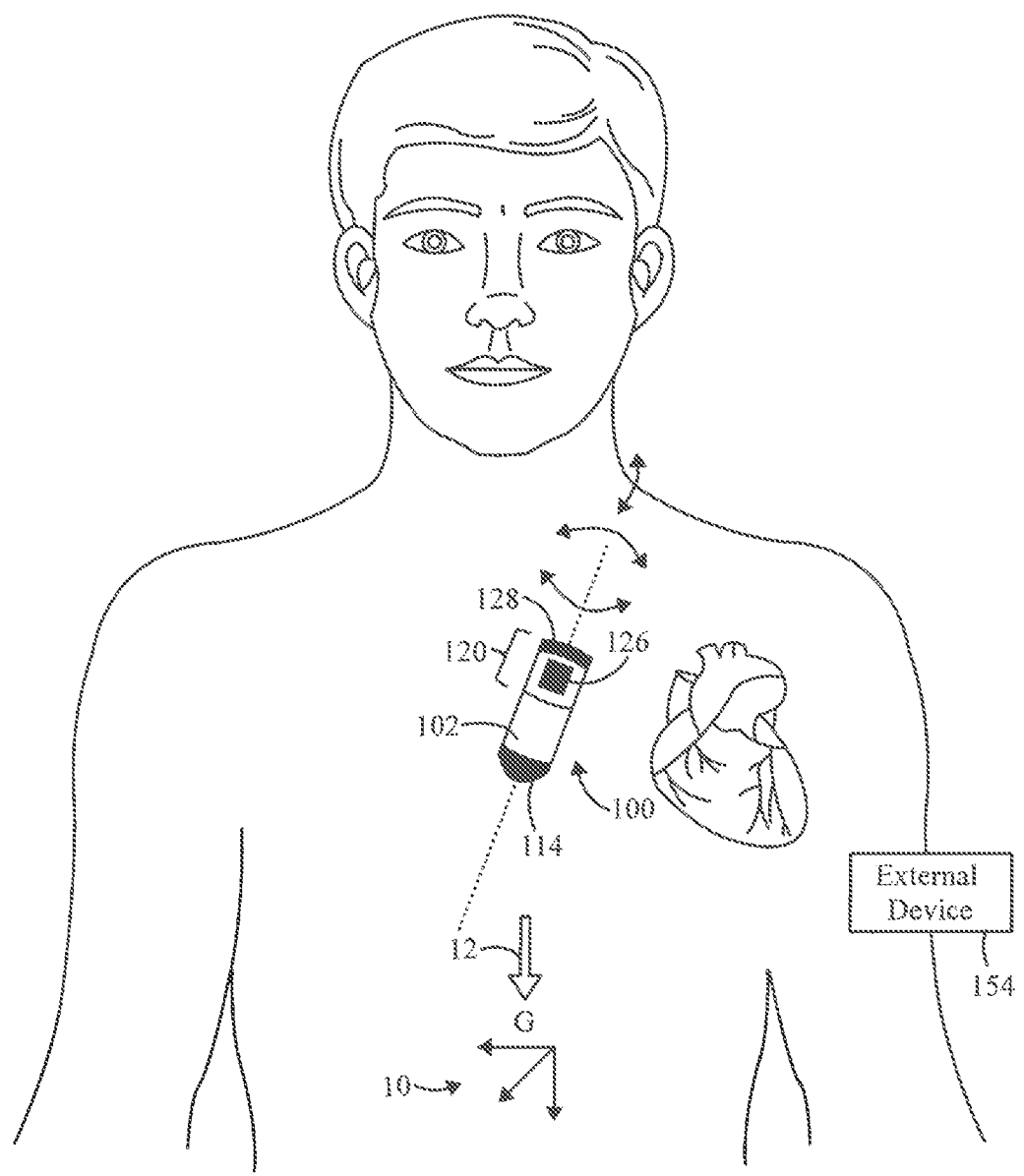
FIG. 1 illustrates an implantable cardiac monitoring device (ICM) intended for subcutaneous implantation at a site near the heart in accordance with embodiments herein.

The terms "state" and "patient state" refer to activity states of a patient, including a stationary state, rest state, exercise state, walking state, and the like.

The terms "posture" and "patient posture" refer to posture positions of a patient, including a standing posture, sitting posture, supine posture, prone posture, horizontal side posture (e.g., laying on one's side) and the like.

The term "IMD location" refers to a position of an IMD, with respect to a reference position, and an orientation of the IMD with respect to a reference orientation. The reference position and orientation may be relative to a global coordinate system. By way of example, an IMD may translationally drift along one or more linear axis (e.g., X, Y and Z directions) from the reference position. Additionally or alternatively, the IMD may rotationally drift along one or more rotational axis (e.g., pitch, yaw and roll directions) from the reference orientation.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes.

The phrase "in connection with treating a heart condition" and similar phrases, as used herein include, but are not limited to, delivering an electrical stimulation or drug therapy to a heart condition. By way of example, treating a heart condition may include, in whole or in part, i) identifying a progression of heart failure over time; ii) confirming an arrhythmia identified by an arrhythmia detection process; iii) instructing the patient to perform a posture recalibration procedure and/or iv) delivering a therapy.

The terms "beat" and "cardiac event" are used interchangeably and refer to both normal and/or abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, a unhealthy or abnormal functioning of the heart.

The term "real-time" refers to a time frame contemporaneous with normal or abnormal episode occurrences. For example, a real-time process or operation would occur during or immediately after (e.g., within minutes or seconds after) a cardiac event, a series of cardiac events, an arrhythmia episode, and the like.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the ICM and a local external device, and/or iii) receiving the data, signals, information, etc. at a remote server over a network connection. The obtaining operation, when from the perspective of an ICM, may include sensing new signals in real time, and/or accessing memory to read stored data, signals, information, etc. from memory within the ICM. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The terms "device shift" and "IMD shift," as used herein, refer to a change in position and/or orientation of an IMD within a subcutaneous implant region. By way of example, an IMD drift may occur when an IMD moves in one or more of six degrees of freedom within the subcutaneous implant region. As a further example, a reference point and/or longitudinal axis of an IMD may move in an X, Y and/or Z direction and/or rotate in a pitch, yaw and/or tilt direction with respect to a reference point in a patient (e.g., a reference point on the heart).

Embodiments may be implemented in connection with one or more implantable medical devices (IMDs), that include an ICM functionality. Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

FIG. 1 illustrates an implantable cardiac monitoring device (ICM) 100 intended for subcutaneous implantation at a site near the heart. The ICM 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the ICM 100, while the electrode 126 is located on a proximal side of the ICM 100. Additionally or alternatively, electrodes 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the AF detection algorithm described herein, a loop memory for temporary storage of CA data, a device memory for long-term storage of CA data upon certain triggering events, such as AF detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The ICM 100 may be configured to be activated by the patient or automatically activated, in connection with recording subcutaneous ECG signals.

The ICM 100 senses far field, subcutaneous CA signals, processes the CA signals to detect arrhythmias and if an arrhythmia is detected, automatically records the CA signals in memory for subsequent transmission to an external device 154. The CA signal processing and AF detection is provided for, at least in part, by algorithms embodied in or implemented by one or more microprocessors in the ICM 100. The ICM 100 includes one or more processors and memory that stores program instructions directing the processors to implement AF detection utilizing an onboard R-R interval irregularity (ORI) process that analyzes cardiac activity signals collected over one or more sensing channels.

The ICM 100 is implanted in a position and orientation such that, when the patient stands, the ICM 100 is located at a reference position and orientation with respect to a global coordinate system 10 that is defined relative to a gravitational direction 12. For example, the gravitational direction 12 is along the Z-axis while the X-axis is between the left and right arms.

As explained herein, the ICM 100 includes electrodes that collect cardiac activity (CA) signals in connection with multiple cardiac beats and in connection with different IMD locations (e.g., different positions and/or different orientations). The ICM may change location within a subcutaneous pocket relative to an initial implant position through translation and/or rotation, such as i) moving up and down (elevating/heaving) within the subcutaneous pocket; ii) moving left and right (strafing/swaying); iii) moving forward and backward (walking/surging); iv) swiveling left and right (yawing); v) tilting forward and backward (pitching); and pivoting side to side (rolling). The ICM 100 also includes one or more sensors to collect device location information indicative of movement of the ICM 100 along one or more degrees of freedom, namely translational motion along X, Y, and Z directions, and/or rotationally motion along pitch, yaw and/or roll directions.

The ICM 100 includes one or more sensors to collect acceleration signatures that are indicative of heart sounds produced at different points in a cardiac cycle. One or more processors of the ICM group the acceleration signatures associated with first and second sets of cardiac beats into a corresponding posture bin based on the device location information. The processors of the ICM identify at least one of differences and/or similarities between the acceleration signatures in a first posture bin (and/or other posture bins) in connection with treating a heart condition.

Figure 2:
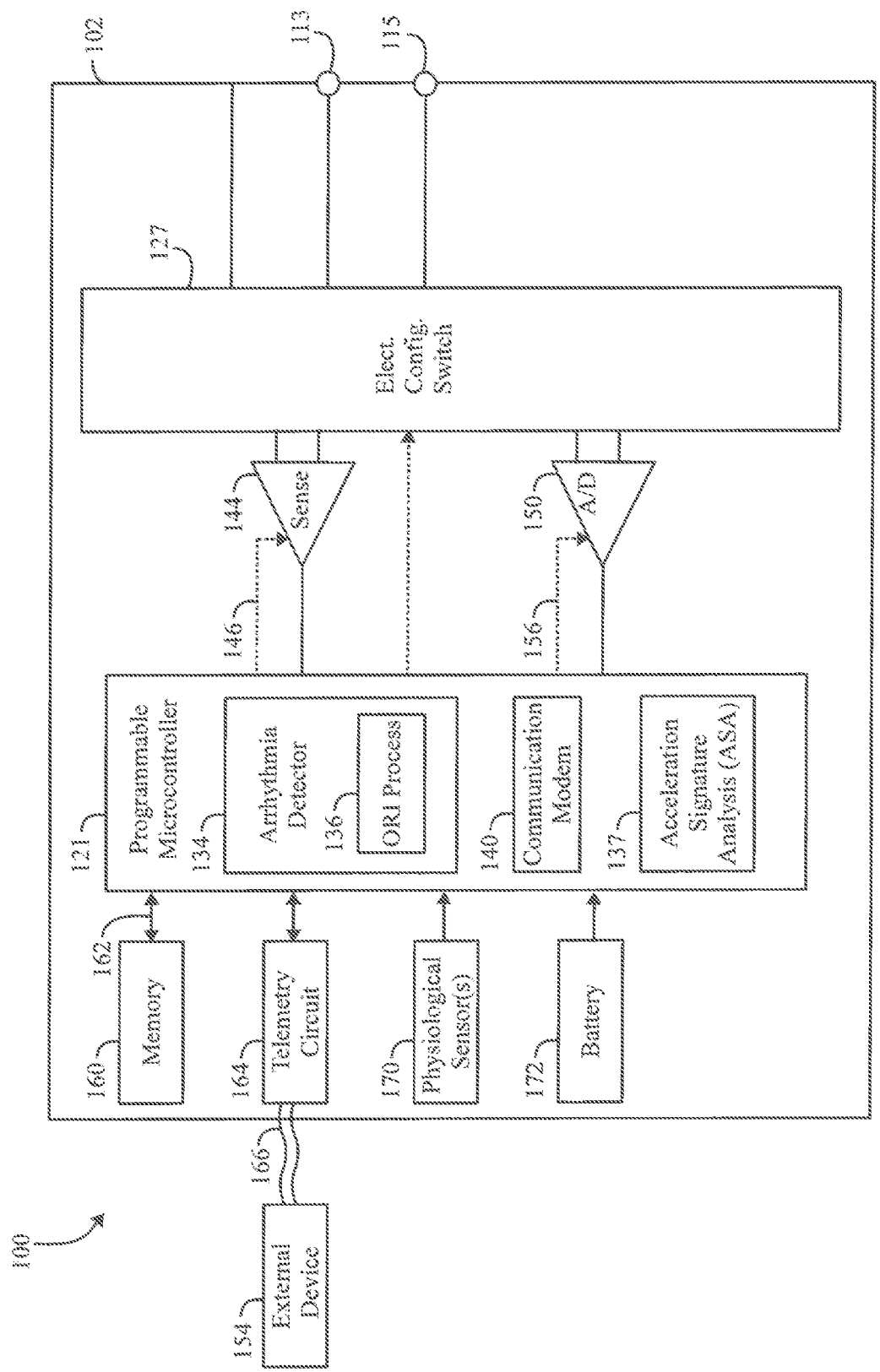
FIG. 2 illustrates a block diagram of the ICM formed in accordance with embodiments herein.

FIG. 2 shows a block diagram of the ICM 100 formed in accordance with embodiments herein. The ICM 100 may be implemented to monitor ventricular activity alone, or both ventricular and atrial activity through sensing circuit. The ICM 100 has a housing 102 to hold the electronic/computing components. The housing 102 (which is often referred to as the "can," "case," "encasing," or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with collecting cardiac activity data and analyzing the cardiac activity data to identify AF episodes.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal from the microcontroller 121. Optionally, the switch 127 may be omitted and the I/O circuits directly connected to the housing electrode 114 and a second electrode 126. Microcontroller 121 includes an arrhythmia detector 134 that is configured to analyze cardiac activity signals to identify potential AF episodes as well as other arrhythmias (e.g., Tachycardias, Bradycardias, Asystole, etc.). By way of example, the arrhythmia detector 134 may implement an AF detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies.

The ICM 100 is further equipped with a communication modem (modulator/demodulator) 140 to enable wireless communication. In one implementation, the communication modem 140 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuit 144 selectively coupled to one or more electrodes that perform sensing operations, through the switch 127 to detect cardiac activity data indicative of cardiac activity. The sensing circuit 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches.

The output of the sensing circuit 144 is connected to the microcontroller 121 which, in turn, determines when to store the cardiac activity data of CA signals (digitized by the A/D data acquisition system 150) in the memory 160. For example, the microcontroller 121 may only store the cardiac activity data (from the A/D data acquisition system 150) in the memory 160 when a potential AF episode is detected. The sensing circuit 144 receives a control signal 146 from the microcontroller 121 for purposes of controlling the gain, threshold, polarization charge removal circuitry (not shown), and the timing of any blocking circuitry (not shown) coupled to the inputs of the sensing circuit.

In the example of FIG. 2, a single sensing circuit 144 is illustrated. Optionally, the ICM 100 may include multiple sensing circuits, similar to sensing circuit 144, where each sensing circuit is coupled to two or more electrodes and controlled by the microcontroller 121 to sense electrical activity detected at the corresponding two or more electrodes. The sensing circuit 144 may operate in a unipolar sensing configuration or a bipolar sensing configuration. Optionally, the sensing circuit 144 may be removed entirely, and the microcontroller 121 perform the operations described herein based upon the CA signals from the A/D data acquisition system 150 directly coupled to the electrodes.

The arrhythmia detector 134 of the microcontroller 121 includes an on-board R-R interval irregularity (ORI) process 136 that detects AF episodes using an automatic detection algorithm that monitors for irregular ventricular rhythms that are commonly known to occur during AF. For example, the ORI process 136 may implement the AF detection methods described in U.S. Pat. No. 8,135,456, titled "Device and Method for Detecting Atrial Fibrillation" the complete subject matter of which is incorporated herein by reference in its entirety.

Optionally, the microcontroller 121 may also include an acceleration signature analysis (ASA) process 137 configured to implement one or more of the operations discussed herein.

The ASA process is configured to be a computer implemented method for detecting arrhythmias in cardiac activity is provided. The method is under control of one or more processors that is configured with specific executable instructions. The method obtains cardiac activity (CA) signals, at electrodes of an ICM, in connection multiple cardiac beats and connection with different ICM orientations relative to gravitational force. The method obtains acceleration signatures, at a sensor of the ICM, indicative of heart sounds generated during the cardiac beats and obtains device location information, at the ICM, with respect to the gravitational force during the cardiac beats. The method groups the acceleration signatures associated with first and second sets of cardiac beats into a corresponding one of first and second posture bins based on the device location information and identifies a difference between the acceleration signals in the first posture bin in connection with treating a heart condition.

Optionally, the method may identify at least one of differences or similarities between the acceleration signals in the second posture bin in connection with treating the heart condition. The method may treat the heart condition by at least one of: i) identifying a progression of heart failure over time; ii) confirming an arrhythmia identified by an arrhythmia detection process; iii) instructing the patient to perform a recalibration procedure and/or iv) delivering a therapy. The method may detect an arrhythmia, may determine whether a current patient posture has changed based on the device location information and may apply a new parameter value to an arrhythmia detection algorithm where the new parameter value is based on the current patient posture. The method may compare morphology characteristics of interest for acceleration signatures within the first posture bin to a correlation limit and, based on the comparing operation, may declare an ICM drift condition.

Optionally, the method may further determine when the morphology characteristics of interest associated with the first posture bin differ from one another by more than a correlation limit. When the correlation limit is exceeded, the declaring operation may comprise setting an ICM drift flag to and on condition. First and second posture bins may correspond to θ first and second body postures, respectively. The determining operation may compare the acceleration signatures in the first posture bin to one another and may comparing the acceleration signatures in the second posture bin to one another to identify a progression of heart failure over time. The determining operation may avoid comparing acceleration signatures from the first posture bin with acceleration signatures from the second posture bin. The grouping operation may comprise grouping a first set of acceleration signatures.

Optionally, the method may further comprise grouping and storing the acceleration signatures into the first and second posture bins for corresponding body postures and for corresponding heart rate ranges. The determining of the heart condition may be based in part on changes in heart sounds within the acceleration signatures for a first body posture and a first heart rate range. The difference may correspond to a difference in at least one of an S1 amplitude, an S1 frequency, or a peak to peak timing between heart sounds in the acceleration signatures. The method may assign the cardiac beats associated with a first posture to the first posture bin, and assigning the cardiac beats associated with a second posture to the second posture bin.

The ICM 100 further includes an analog-to-digital A/D data acquisition system (DAS) 150 coupled to one or more electrodes via the switch 127 to sample cardiac activity signals across any pair of desired electrodes. The data acquisition system 150 is configured to acquire cardiac electrogram (EGM) signals as CA signals, convert the raw analog data into digital data, and store the digital data as CA data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential AF episodes. The ASA process 137 may be applied to signals from the sensor circuit 144 and/or the DAS 150.

By way of example, the external device 154 may represent a bedside monitor installed in a patient's home and utilized to communicate with the ICM 100 while the patient is at home, in bed or asleep. The external device 154 may be a programmer used in the clinic to interrogate the ICM 100, retrieve data and program detection criteria and other features. The external device 154 may be a handheld device (e.g., smartphone, tablet device, laptop computer, smartwatch and the like) that can be coupled over a network (e.g., the Internet) to a remote monitoring service, medical network and the like. The external device 154 facilitates access by physicians to patient data as well as permitting the physician to review real-time CA signals while collected by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, AF detection criteria, activity sensing or other physiological sensors, and electrode polarity, etc.

In addition, the memory 160 stores the acceleration signatures, device location information, posture bins, reference posture data sets, cardiac activity signals, as well as the markers and other data content associated with detection of arrhythmia episodes. For example, the memory 160 may store the groupings of the acceleration signatures for various sets of cardiac events that are sorted into corresponding posture bins based on the device location information. The operating parameters of the ICM 100 may be non-invasively programmed into the memory 160 through a telemetry circuit 164 in telemetric communication via communication link 166 with the external device 154. The telemetry circuit 164 allows intracardiac electrograms and status information relating to the operation of the ICM 100 (as contained in the microcontroller 121 or memory 160) to be sent to the external device 154 through the established communication link 166. In accordance with embodiments herein, the telemetry circuit 164 conveys the cardiac activity data, markers and other information related to AF episodes.

The ICM 100 may further include magnet detection circuitry (not shown), coupled to the microcontroller 121, to detect when a magnet is placed over the unit. A magnet may be used by a clinician to perform various test functions of the housing 102 and/or to signal the microcontroller 121 that the external device 154 is in place to receive or transmit data to the microcontroller 121 through the telemetry circuits 164.

The ICM 100 can further include one or more physiologic sensors 170. For example, the physiologic sensor 170 may represent one or more accelerometers, such as a three dimensional (3D) accelerometer. The sensor 170 may utilize a piezoelectric, a piezoresistive, and/or capacitive components are commonly used to convert the mechanical motion of the 3D accelerometer into an electrical signal received by the microcontroller 121. By way of example, the 3-D accelerometer may generate three electrical signals indicative of motion in three corresponding directions, namely X, Y and Z directions. The electrical signals associated with each of the three directional components may be divided into different frequency components to obtain different types of information therefrom.

In accordance with embodiments herein, the microcontroller 121 isolates and analyzes a DC-low frequency component from each of the three electrical signals corresponding to motion in three respective directions. For example, the DC-low frequency component may include signals having a frequency of 0-100 Hz, and more preferably in the range of 10-100 Hz. The three directional signals generated by the 3-D accelerometer may be passed through a low-pass filter to separate the DC-low frequency component. The output of the low-pass filter, including primarily only DC-low frequency components, is representative of device location information which is analyzed by the microcontroller 121 as described herein. The microcontroller receives, from the low-pass filters, a first DC-low frequency component providing location information in the X direction, a second DC-low frequency component providing location information in the Y direction and a third DC-low frequency component providing location information in the Z direction.

The physiologic sensors 170 collects device location information with respect to gravitational force while the ICM collects cardiac activity signals in connection with multiple cardiac beats. The microcontroller 121 may utilize the signals from the physiologic sensor 170 in the manner described in U.S. Pat. No. 6,937,900, titled "AC/DC Multi-Axis Accelerometer For Determining A Patient Activity And Body Position," the complete subject matter which is expressly incorporated herein by reference. While shown as being included within the housing 102, the physiologic sensor(s) 170 may be external to the housing 102, yet still, be implanted within or carried by the patient.

The physiologic sensor 170 may be further configured to obtain acceleration signatures indicative of heart sounds generated during cardiac beats. The acceleration signatures from the sensor 170 are provided to the microcontroller 121 and are analyzed by the acceleration signature analysis process 137. For example, the accelerator signatures may be an AC-high frequency component from the 3-D accelerometer. The AC-high frequency component may represent a composite AC-high frequency component formed from a combination (e.g., a sum) of the AC-high frequency components from the three electrical signals. The composite AC-high frequency component generally represents the acceleration signature that is indicative of heart sounds produced during a corresponding cardiac cycle. The AC-high frequency component may include signals having a frequency of 10 KHz or more, and more preferably in the range of 10-100 kHz. The three directional signals generated by the 3-D accelerometer may be passed through a high-pass filter to separate the AC-high frequency component. The output of the high-pass filter, including primarily only AC-high frequency components, represents an acceleration signature indicative of heart sounds produced during a corresponding cardiac cycle.

Additionally or alternatively, the ICM 100 may include a separate heart sound sensor that is configured to collect the acceleration signatures indicative of heart sounds.

Figure 3:
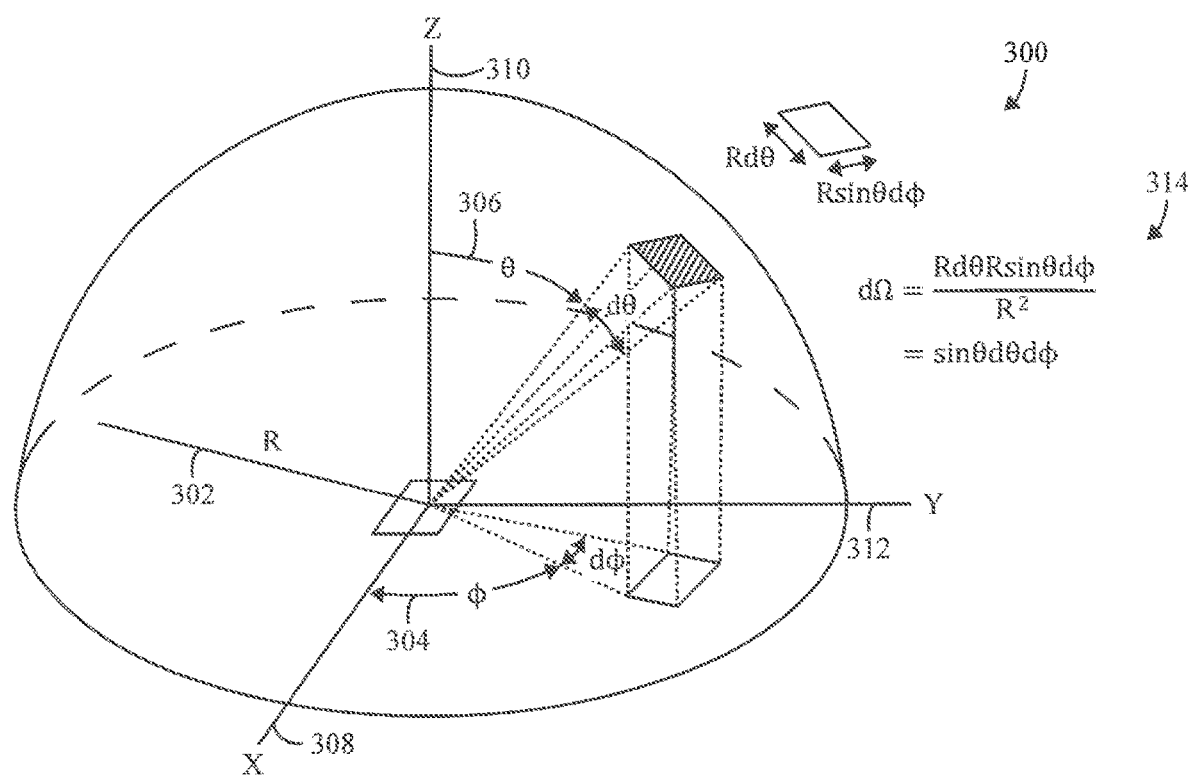
FIG. 3 illustrates force vectors experienced by the ICM in accordance with embodiments herein.

FIG. 3 illustrates force vectors experienced by the ICM 100. The microcontroller 121 utilizes device location information, collected from the physiologic sensor 170, to define a base local device coordinate system 300 for the ICM. The base local device coordinate system 300 may correspond to a global coordinate system and may be defined in terms of various types of coordinate systems, such as a Cartesian coordinate system, Polar coordinate system or otherwise. The microcontroller 121 defines the base local device coordinate system 300 relative to a reference vector 302 that corresponds to and is defined by, the gravitational force of earth. Regardless of the position and orientation of the ICM 100, the gravitational force of earth will remain constant and serve as a reference vector having a fixed magnitude and direction.

After implant, during a calibration procedure, a patient moves through a number of predefined postures that are configured to orient the ICM 100 in known positions and orientations with respect to the gravitational force. When the patient is at each of the predefined postures, the microcontroller 121 collects device location information from the physiologic sensor 170, namely measurements for the first, second and third DC-low frequency components providing location information in the X, Y and Z directions, relative to the Earth's gravitational force. Based on the first, second and third DC-low frequency components, the microcontroller 121 defines the base local device coordinate system 300 having X, Y and Z axes 308, 310 and 312. The ICM 100 will have an initial/reference position and orientation within the base local device coordinate system 300. For example, the initial reference position and orientation may define an orientation of a longitudinal axis extending through a center of the ICM 100 and may define a position of a reference point on the ICM 100 (e.g., a distal or proximal tip, a center of mass, a center point on a select electrode and the like). During the calibration procedure, the microcontroller 121 defines a reference position and reference orientation for the ICM 100 relative to the local base local device coordinate system 300 and/or global coordinate system. The microcontroller 121 calculates reference orientation angles Θ306, φ304 in a 3-D polar coordinate system based on the first, second and third DC-low frequency components.

At each predefined posture, the microcontroller 121 calculates a reference posture data set that includes the reference orientation angles θ306, φ304 calculated from the DC-low frequency components. The reference posture data set also includes a posture related impedance ΔΩ calculated based on the set of reference orientation angles θ306, φ304. The posture related impedance ΔΩ is calculated according to the equation 314: $\Delta\Omega=(Rd\Theta R \sin \Theta d\phi)/R^2$, which may be simplified to $\Delta\Omega=\sin\Theta d\Theta d\phi$, where R represents the vector for gravitational force and Θ and φ represent the reference orientation angles 306, 304. The set of reference coordinate angles, posture related impedance, and posture position/orientation are stored at calibration for each predefined posture as corresponding reference posture data sets.

Once the calibration procedure is completed, the microcontroller 121 monitors the output of the physiologic sensor 170 for indications of activity. When AC signals from the physiologic sensor 170 indicate activity, the microcontroller 121 collects new DC-low frequency components and analyzes the DC-low frequency components to determine if a posture change has occurred. When a posture change occurs, the microcontroller 121 implements various algorithms and processes as described herein, including algorithms adapted to detect and confirm arrhythmias. Additionally or alternatively, the microcontroller 121 may continuously or periodically monitor output signals from the physiologic sensor 170 to collect and analyze DC-low frequency components as described herein.

When the ICM 100 moves, the physiologic sensor 170 outputs device location information, in the form of changes in the DC-low frequency components that are analyzed by the microcontroller 121 to identify change in the angles θ306, φ304. Changes in the DC-low frequency components may indicate a change in the angles based on an orientation of the ICM 100, such as changes in orientation, rotation, or translational position of the ICM 100. Additionally or alternatively, when the orientation angles θ306, φ304 change from prior measured orientation angles θ306, φ304, the microcontroller 121 may set a "device rotation or motion" flag to an ON condition.

Returning to FIG. 2, a battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The battery 172 may afford various periods of longevity (e.g., three years or more of device monitoring). In alternate embodiments, the battery 172 could be rechargeable. See, for example, U.S. Pat. No. 7,294,108, titled "Cardiac event micro-recorder and method for implanting same", which is hereby incorporated by reference.

The ICM 100 provides a simple to configure data storage option to enable physicians to prioritize data based on individual patient conditions, to capture significant events and reduce the risk that unexpected events are missed. The ICM 100 may be programmable for pre- and post-trigger event storage. For example, the ICM 100 may be automatically activated to store 10-120 seconds of CA data prior to an event of interest and/or to store 10-120 seconds of post CA data. Optionally, the ICM 100 may afford patient triggered activation in which pre-event CA data is stored, as well as post event CA data (e.g., pre-event storage of 1-15 minutes and post-event storage of 1-15 minutes). Optionally, the ICM 100 may afford manual (patient triggered) or automatic activation for CA data. Optionally, the ICM 100 may afford additional programming options (e.g., asystole duration, bradycardia rate, tachycardia rate, tachycardia cycle count). The amount of CA data storage may vary based upon the size of the memory 160. When the ICM 100 is activated to store CA data, the ICM 100 also collects acceleration signatures for the cardiac beats within the CA data, and optionally, device location information indicative of a position and orientation of the ICM 100.

The ICM 100 may provide comprehensive safe diagnostic data reports including a summary of heart rate, in order to assist physicians in diagnosis and treatment of patient conditions. By way of example, reports may include episodal diagnostics for auto trigger events, episode duration, episode count, episode date/time stamp and heart rate histograms. The ICM 100 may be configured to be relatively small (e.g., between 2-10 cc in volume) which may, among other things, reduce the risk of infection during the implant procedure, afford the use of a small incision, afford the use of a smaller subcutaneous pocket and the like. The small footprint may also reduce implant time and introduce less change in body image for patients.

Figure 4A:
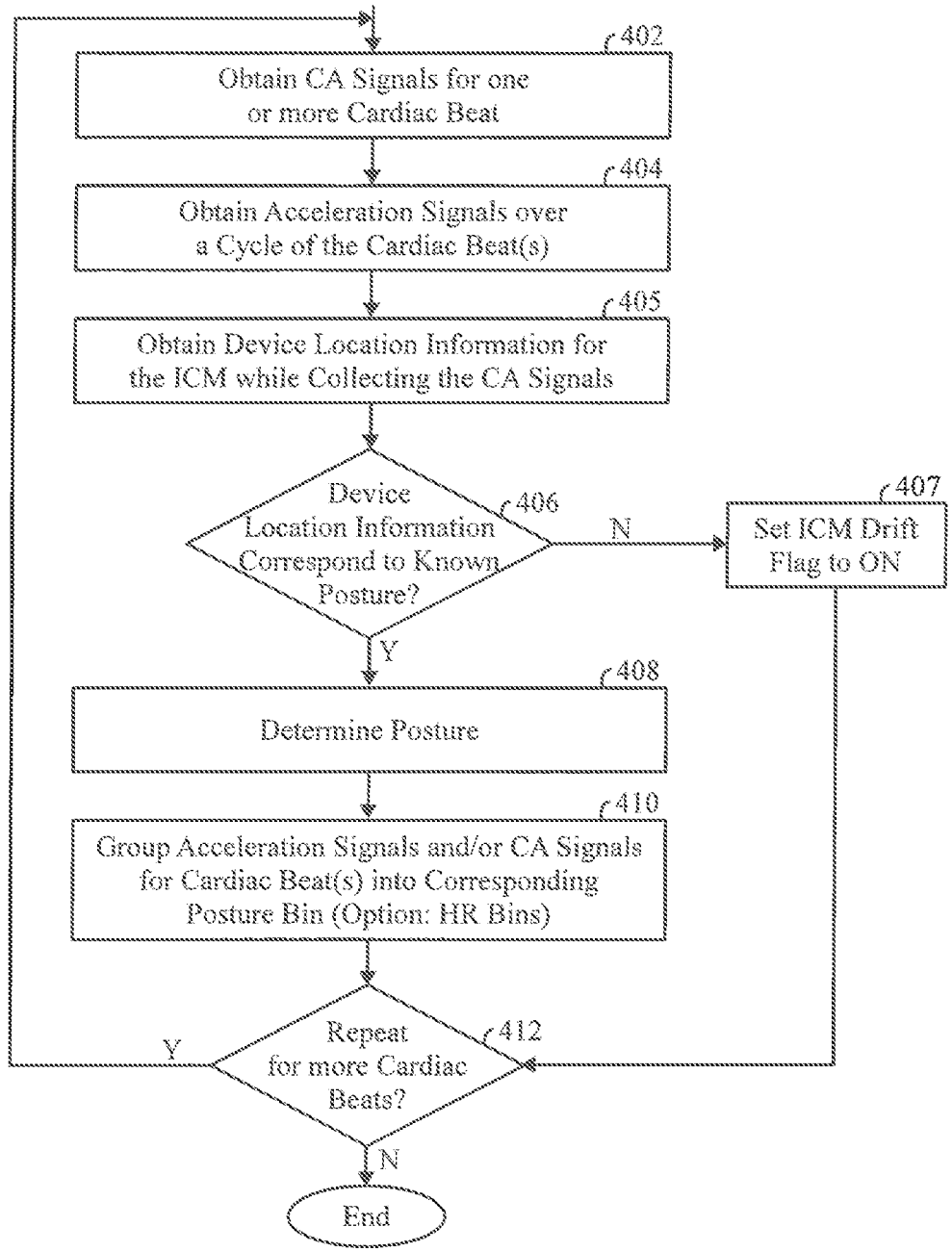
FIG. 4A illustrates a process for managing collection of CA signals in connection with acceleration signatures and device location information in accordance with embodiments herein.

FIG. 4A illustrates a process for managing collection of CA signals in connection with acceleration signatures and device location information in accordance with embodiments herein. All or a portion of the operations of FIG. 4A may be implemented by one or more processors in the ICM, one or more processors of the local external device and/or one or more processors of a remote server. Optionally, the operations of FIG. 4A may be divided between the IMD, local external device and remote server.

At 402, the one or more processors obtain CA signals for one or more cardiac beats. For example, the CA signals may be obtained by sensing and collecting the CA signals at one or more combinations of electrodes provided on the housing of the IMD. As explained herein, as the position and/or orientation of the IMD changes from an initial implant reference position, the position and/or orientation of the electrodes mounted on the housing of the IMD similarly change, thereby potentially causing changes in the CA signals.

At 404, the one or more processors obtain acceleration signatures over a cycle of the one or more cardiac beats for which CA signals were collected at 402. For example, the acceleration signatures may be collected over a single cardiac beat such that the acceleration signature is indicative of the S1, S2, S3, and S4 heart sounds for one cardiac cycle. The processors are electrically coupled to a heart sound sensor, such as the physiologic sensor 170 (e.g., a 3D accelerometer). The acceleration signature includes signals indicative of at least one heart sound (e.g., S1 Contraction, S2 Relaxation, S3 Blood flowing into the ventricle, S4 Hypertension) of the subject. A heart sound of the subject can include an audible or mechanical noise or vibration indicative of blood flow through the heart or valve closures of the heart.

At 405, the one or more processors obtain device location information indicative of a position and/or orientation of the IMD with respect to a reference position and reference orientation. By way of example, the device location information may be obtained with respect to a gravitational force experienced by the IMD.

At 406, the one or more processors determine whether the device location information (DLI) correspond to a known posture. For example, the processors may determine whether the values for the orientation angles θ, φ fall within one or more predetermined ranges for the orientation angles θ, φ. Additionally or alternatively, the processors may determine whether the DLI corresponds to a known posture based on whether a posture related impedance falls within one or more predetermined impedance ranges. When the DLI does not correspond to a known posture, flow moves to 407.

At 407, the one or more processors determined that the IMD may have drifted within the patient, such that the physical position and orientation of the IMD have changed within the subcutaneous pocket relative to the prior position and orientation at the time of implant and/or at a later calibration time. At 407, the processors set an IMD drift flag to an ON state thereby indicating that the IMD may have experience drift.

Alternatively, at 406, when processors determine that the DLI corresponds to a known posture, flow moves to 408.

At 408, the one or more processors analyze the device location information to determine an IMD posture. The IMD posture determined by the processors is generally indicative of and corresponds to, known patient postures. For example, during a calibration operation, reference positions and reference orientations are defined for the IMD as corresponding to predetermined patient postures. Changes in the position and orientation of the IMD can then be interpreted by the processors to correspond to changes in the IMD posture and patient posture. The relation between IMD posture and patient posture remains constant and known to the IMD, provided that the IMD does not drift in position or orientation within the subcutaneous implant pocket. As non-limiting examples, the processors may determine that the device location information is indicative of an IMD posture corresponding to a seated posture, standing posture, prone posture, supine posture and the like.

Optionally, each patient posture may correspond to a range of positions and orientations for the IMD. For example, when the device location information indicates that the IMD is aligned within a range of orientations, the processors may designate a single common posture for any orientation within the range of orientations. The processors may determine the posture based on the device location information collected during a single cardiac beat. Additionally or alternatively, the processors may collect a mean and/or the ensemble of device location information over time and use the mean/ensemble to determine the posture of the patient.

Optionally, the determination of posture at 408 may be performed before the decision at 406. For example, the processors may determine a posture indicated by the DLI (at 408) and then determine (at 406) whether the posture corresponds to a known posture.

At 410, the one or more processors group the acceleration signals and/or CA signals for the cardiac beat(s) into a corresponding posture bin for the posture determined at 408. Additionally or alternatively, the processors may group the acceleration signals and/or CA signals for the cardiac beat(s) into a corresponding heart rate bin associated with the current heart rate. For example, when posture bins and heart rate bins are used in combination, an individual acceleration signal may be grouped with other acceleration signals (for prior cardiac beats) that were collected while the patient exhibited a similar heart rate (e.g., within a predetermined heart rate range corresponding to the heart rate bins) and that were collected while the patient was in a similar posture.

At 412, the one or more processors determine whether to repeat the operations for more cardiac beats. If so, flow returns to 402. Otherwise, the process of FIG. 4A ends.

The operations of FIG. 4A build sets of acceleration signatures associated with each posture bin. As explained herein, the acceleration signatures for a correspond posture bin are analyzed to identify differences and similarities therebetween in connection with treating a heart condition.

Figure 4B:
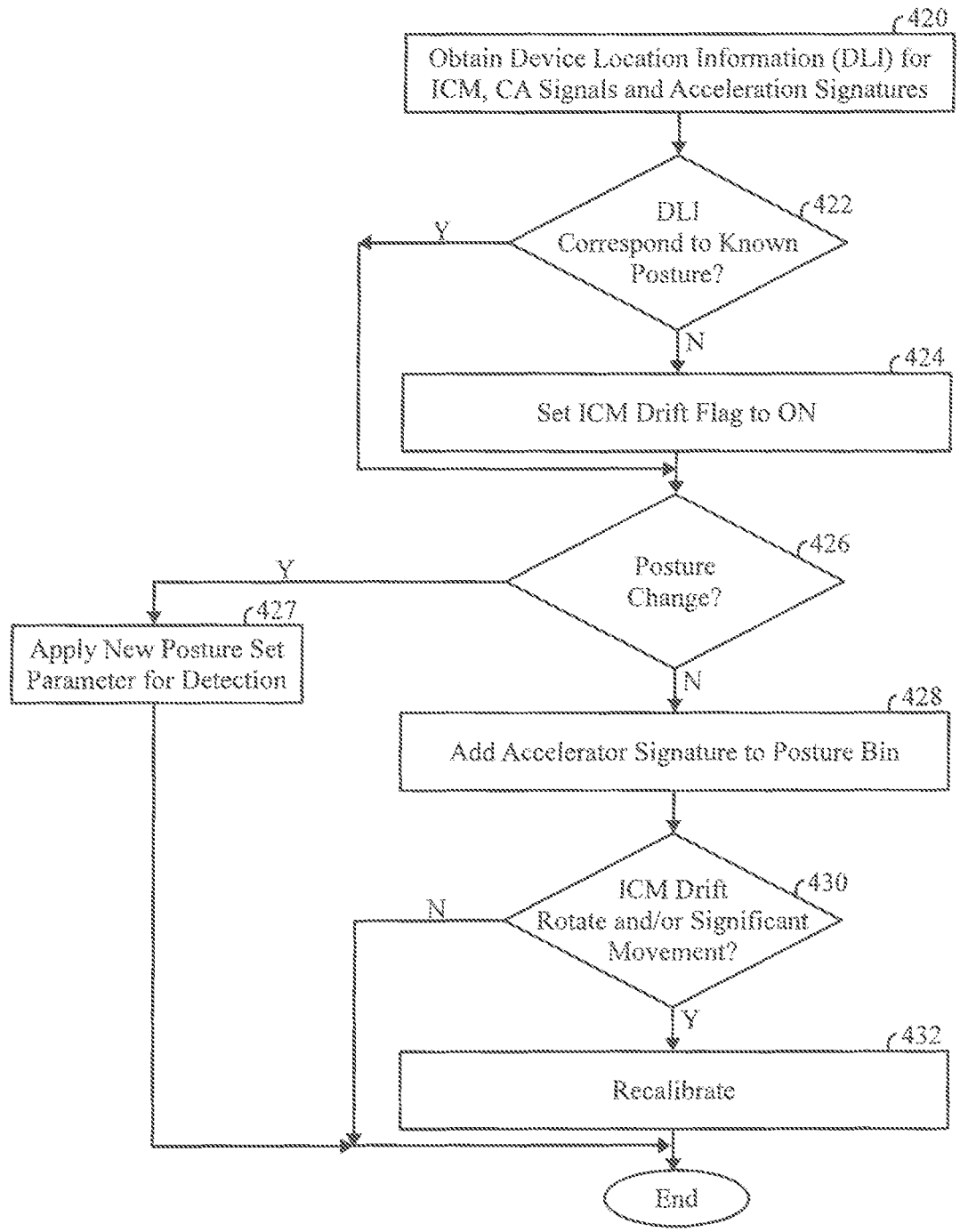
FIG. 4B illustrates a process for detecting ICM drift in accordance with embodiments herein.

FIG. 4B illustrates a process for detecting IMD drift in accordance with embodiments herein. At 420, the one or more processors obtain device location information (DLI) indicative of a position and/or orientation of the IMD with respect to a reference position and reference orientation. The one or more processors also obtain acceleration signatures over a cycle of the one or more cardiac beats for which CA signals were collected, and obtain the CA signals for the one or more cardiac beats.

At 422, the one or more processors determine whether the DLI corresponds to a known posture. For example, the processors may determine whether the values for the orientation angles θ, φ fall within one or more predetermined ranges for the orientation angles θ, φ. Additionally or alternatively, the processors may determine whether the DLI corresponds to a known posture based on whether a posture related impedance falls within one or more predetermined impedance ranges. Additionally or alternatively, the processors may determine a posture from the DLI and determine whether the prosture corresponds to a known posture. When the DLI corresponds to a known posture, flow skips to 426. Otherwise, when the DLI does not correspond to a known posture, flow continues to 424.

At 424, the one or more processors determine that the IMD may have drifted within the patient, such that the physical position and orientation of the IMD have changed within the subcutaneous pocket relative to the prior position and orientation at the time of implant and/or at a later calibration time. At 424, the processors set an IMD drift flag to an ON state thereby indicating that the IMD may have experience drift.

At 426, the one or more processors determine whether a posture change has occurred. When a posture changes identified at 426, flow moves to 427. Alternatively, when a posture change does not occur, flow continues to 428.

At 427, the one or more processors apply a new set of detection parameters for the device when the posture is known. Alternatively, when the posture is unknown, the process of FIG. 4B may end.

At 428, the one or more processors add the acceleration signature to a current corresponding posture bin, when a posture bin is known. Optionally, if no posture bin is known, a new posture bin may be created and the acceleration signature added to the new posture bin. Optionally, if no posture bin is known, the operation at 428 may be skipped.

Figure 6:
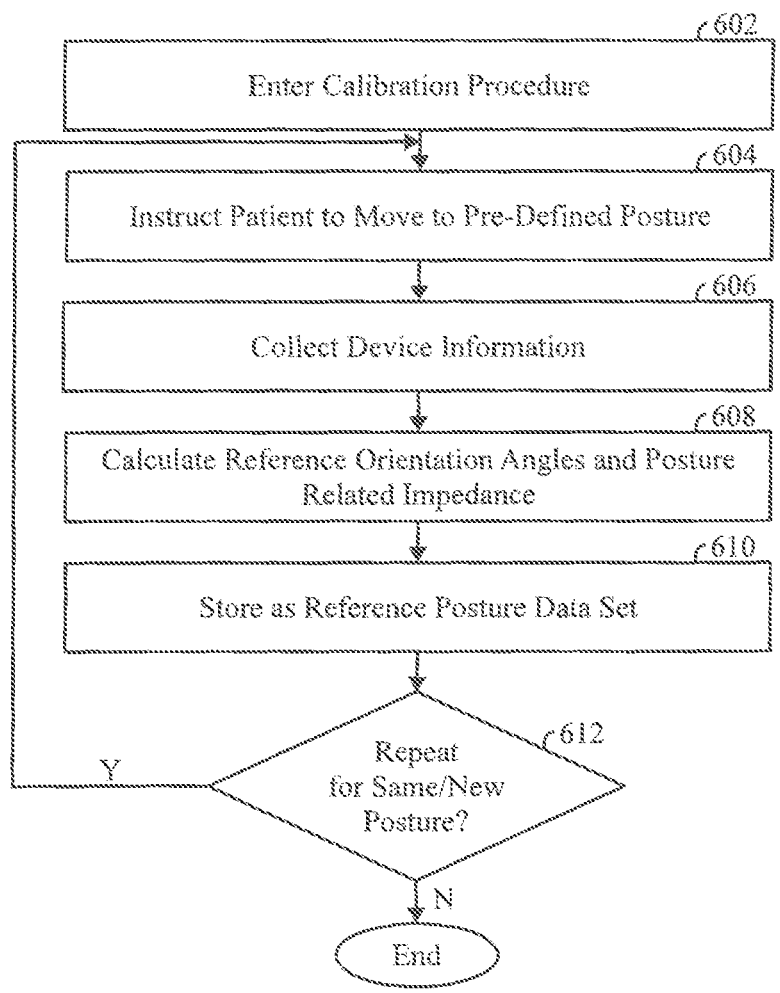
FIG. 6 illustrates a posture calibration process implemented in accordance with embodiments herein.

At 430, the one or more processors determine whether IMD drift corresponds only to rotational movement along or in combination with translation or migration. When the IMD drift includes rotational movement, flow continues to 432. At 432, the process performs a calibration operation (FIG. 6). Alternatively, when the IMD drift does not include rotational movement, alone or in combination with translation/migration movement, the process of FIG. 4B ends.

Figure 5:
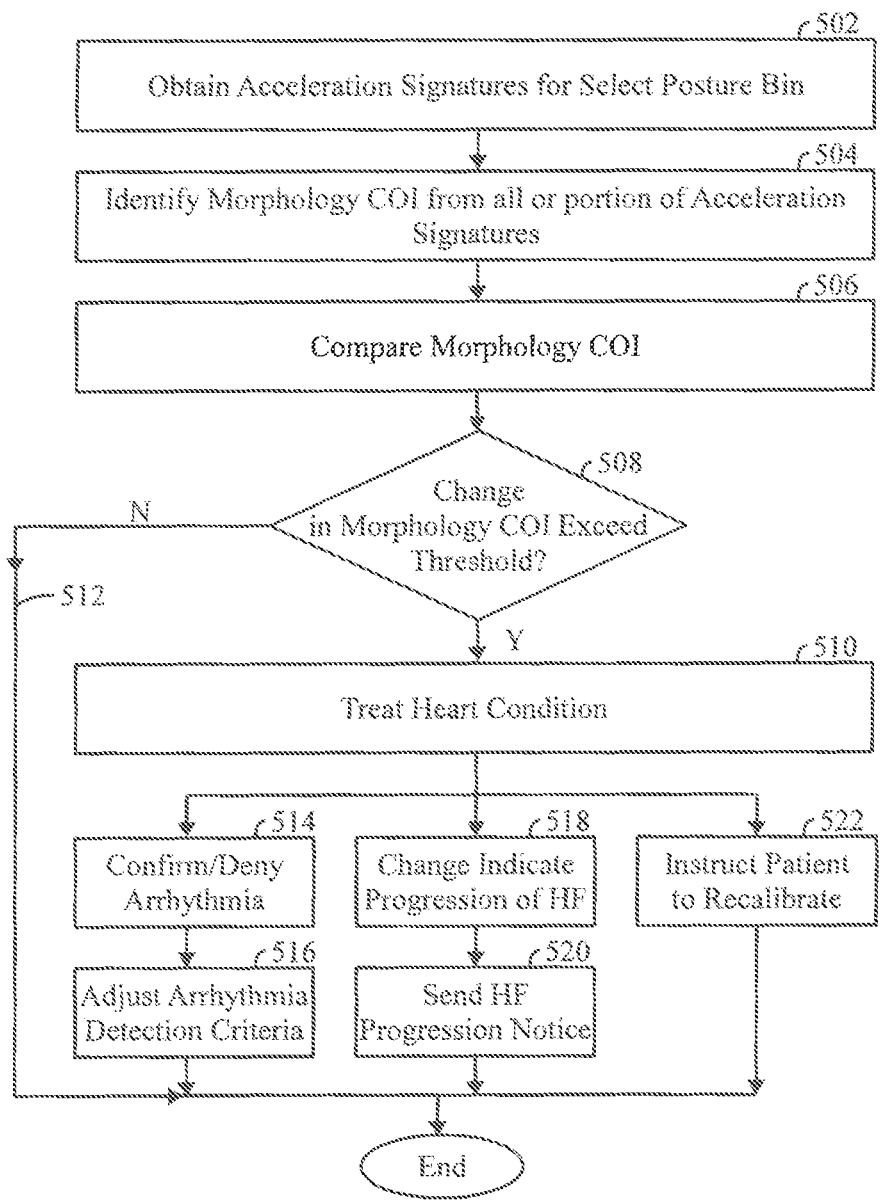
FIG. 5 illustrates a process for analyzing acceleration signatures in one or more posture bins in connection with treating a heart condition in accordance with embodiments herein.

FIG. 5 illustrates a process for analyzing acceleration signatures in one or more posture bins in connection with treating a heart condition in accordance with embodiments herein. At 502, the one or more processors obtain the acceleration signatures for a select posture bin. The processors may select the posture bin based on a current posture exhibited by the IMD. For example, the processors may initiate the process of FIG. 5 each time the processors measure new device location information. The new device location information is used to identify a current posture. The processors select the posture bin corresponding to the current posture.

Additionally or alternatively, the processors may choose to periodically analyze the acceleration signatures for a select posture bin independent of a current cardiac beat. For example, nightly after the patient has gone to sleep, the processors may choose to analyze the acceleration signatures only recorded when a patient was lying in a prone and/or supine position. Additionally or alternatively, while the patient is sleeping and/or at a predetermined time of day, the processors may choose to analyze only the acceleration signatures recorded when a patient was standing. As a further option, the processors may choose the select posture bin based on an activity state. For example, when the patient is in a rest state, the processors may choose to analyze acceleration signatures recorded only while the patient was in a posture of interest and in a resting state.

At 504, the one or more processors identify a morphology characteristic of interest (COI) from the acceleration signatures for the select posture bin. The processors may analyze all of the acceleration signatures within the posture bin and/or only a portion of the acceleration signatures. For example, the morphology COI may include at least one of an amplitude of one or more heart sound in the acceleration signatures, a total energy of the heart sound, a frequency of the heart sound, an interval between heart sound peaks within the acceleration signatures, and/or the like.

To obtain the morphology COI, the processors identify the S1, S2, S3 and S4 heart sounds from the acceleration signature for a current beat. As one example, the processors may temporally align an R-wave marker with the acceleration signature. The R-wave marker is a device documents marker designating a known point in the cardiac cycle (e.g., R-wave peak). The processors may set heart sound capture windows following the R-wave marker by ser times (based on current heart rate). The windows overlay the acceleration signal at times expected to match the S1, S2, etc. heart sounds.

The processors analyze the portions of the acceleration signature from the hear sound capture windows to identify the morphology COI. For example, the first capture window overlays S1 and thus the processors analyze the signal content of the acceleration signature in the first capture window for S1 amplitude, frequency, energy, etc. Optionally, a peak-to-peak interval may be measured between an S1 peak and an S2 peak in the first and second capture windows.

At 506, the one or more processors compare values for the morphology COI from the acceleration signatures. For example, the processors may compare amplitudes of different first heart sound signals S1 collected over time during a standing or prone posture. Additionally or alternatively, the processors may compare peak-to-peak intervals between select heart sounds (e.g., S1 to S2) over multiple cardiac cycles collected in a given posture. Optionally, the heart sound signals may be binned not just based on posture, but also based on heart rate. For example, amplitude, the frequency, the peak to peak, and/or the like of the heart sound signals may vary for different heart rate ranges. Therefore, it may be desirable to limit the comparison at 506 to morphology COIs of acceleration signatures for heart sound signals collected in connection with a desired posture and heart rate range.

At 508, the one or more processors determine whether the morphology COI has changed between the acceleration signatures, and if so whether the change in the morphology COI exceeds a threshold. When the change in morphology COI exceeds the threshold, flow moves to 510. Alternatively, when the morphology COI change does not exceed the threshold, flow moves along path 512. The processors may identify changes in an amplitude of a first heart sound S1 from a series of acceleration signatures over time. For example, more recently acquired S1 signals may exhibit a lower amplitude as compared to previous S1 signals recorded a day earlier, a week earlier, etc. The processors determine the changes in the amplitude between the current S1 signal recording and the previous S1 signal.

It is desirable to limit the comparison at 506 to heart sounds associated with a common posture because the S1 amplitude for a patient standing up or exercising, may be greater than the S1 amplitude when sitting down, and/or the like. In another example, the S1 amplitude may decrease responsive to the patient lying down, lying on a bed, sleeping, and/or the like. By limiting the comparison at 506 to first heart rate sounds S1 associated with a common posture, embodiments herein ensure that the change in S1 amplitude is posture independent, namely not based on posture changes.

Additionally or alternatively, the morphology COI identification and comparison at 504, 506 may be based on a frequency comparison that is posture independent. For example, at 504, the processors may identify one or more primary frequency components (as the morphology COI) of the acceleration signature. For example, a first heart sound S1 component of the acceleration signature may be isolated and analyzed to identify the primary frequency component(s). At 506, the processors compare frequency components of current and prior first heart sounds S1. Changes in the S1 frequency between current and previous S1 signal recordings may be indicative of an arrhythmia or a progression of heart failure. Embodiments herein limit the comparison at 506 to S1 frequencies associated with a common posture as the frequency may increase in response to a patient standing up, exercising and/or the like. In addition, the S1 frequency may decrease in response to the patient lying down, lying on a bed, sleeping, and/or the like.

Additionally or alternatively, the morphology COI identification and comparison at 504, 506 may be based on a peak to peak comparison that is posture independent. For example, at 504, the processors may identify a peak to peak timing of S1 and S2 peaks within a current beat. At 506, the processors compare the S1 and S2 peak to peak timing of current and previous beats. By comparing peak to peak timing between heart sounds that are only associated with a common posture, the process remains posture independently.

At 510, the one or more processors treat the heart condition. The manner in which the heart condition is treated may vary along different or parallel paths as indicated in FIG. 5. For example, the heart condition treatment may move to 514. At 514, the one or more processors confirm or deny an arrhythmia that has been detected by an arrhythmia detection algorithm running in parallel. Next, at 516, the one or more processors may adjust one or more arrhythmia detection criteria that are utilized by the arrhythmia detection algorithm. For example, when an arrhythmia is denied at 514, at 516 the processors may adjust the arrhythmia detection criteria by changing one or more sensitivity parameters of a sensitivity profile utilized by the arrhythmia detection algorithm.

At 518, the one or more processors may analyze the changes in the morphology COI to determine whether the change indicates a progression of heart failure, as all or a portion of the heart condition treatment. When the change in the morphology COI indicates HF progression, at 520, the processors send an HF progression notification. The HF progression notification may be transmitted wirelessly to a local external device and/or a remote server. In response thereto, the patient may be notified of the change, given instructions to take medication, change the prescription and/or schedule an appointment with a physician.

At 522, the one or more processors may instruct a patient to perform a recalibration operation, as all or a portion of the heart condition treatment. For example, the processors may convey a recalibration notification to a local external device that, in response thereto, outputs an instruction to recalibrate to the patient.

Additionally or alternatively, the one or more processors may be housed in a therapy delivery IMD and instruct the IMD to deliver a therapy, as all or a portion of the heart condition treatment.

Optionally, the operations of FIGS. 4A and 5 may be performed in connection with ensembles of beats (e.g., 5-10 beats). For example, the obtaining and grouping operations at 402-410 in FIG. 4A may be performed on an average, mean or other ensemble operation for 5-10 beats. The operations at 502-508 in FIG. 5 may also be performed on an ensemble of beats.

FIG. 6 illustrates a posture calibration process implemented in accordance with embodiments herein. At 602, the one or more processors enter a calibration procedure. For example, a calibration procedure may be entered in response to a patient instruction (e.g., entered at a local external device), in response to a physician instruction (e.g., entered through a programmer or remote physician workstation), in response to an automated instruction from a remote server and the like.

Additionally or alternatively, the calibration procedure may be entered automatically periodically and/or automatically in response to determinations made by the IMD. For example, the IMD may determine that one or more reference posture data sets are no longer accurate and/or are inconsistent with other information collected by the IMD. As an example, a reference posture data set may no longer be considered "consistent" with other "non-posture" information collected by the IMD. A reference posture data set may be considered "inconsistent" or no longer consistent with other information collected by the IMD when one or more characteristics of interest (COI) from the non-posture information exceed a COI correlation limit. Examples of non-posture information include CA signals, device markers, acceleration signatures, activity states, activity signals and the like. For example, the device location information may indicate that the patient is in a prone or supine posture, but the activity signal may indicate that the patient is in an active state and/or exhibits an accelerated heart rate. Further, the device location information may indicate that the patient is maintaining an unusual posture (e.g., a torso substantially tilted to an awkward position, left, right, forward or backward), but the activity signals may indicate that the patient is moving (e.g., in an active state).

Additionally or alternatively, the reference posture data set may no longer be consistent with an acceleration signature collected by the IMD. For example, the IMD may determine that the patient is in a first posture (e.g., prone or supine). When the patient is in the first posture, normally, the IMD would expect to record acceleration signatures having morphologies with certain characteristics of interest that fall within COI correlation limits (e.g., certain peak to peak limits, amplitude limits, frequency content limits, energy content limits, etc.). However, even though the IMD has determined that the IMD "appears" to be in the first posture, the IMD may collect an acceleration signature that is "inconsistent" with the first posture. For example, the collected acceleration signature may include an S1 heart sound component that has a morphology (higher than expected amplitude or energy) more consistent with acceleration signature morphologies previously recorded in connection with a different second posture (e.g., standing). Additionally or alternatively, the IMD make determine that the heart sound morphology, within the acceleration signature, for a combination of one or more of the S1, S2, S3 and S4 heart sound components are associated with a different second posture.

Additionally or alternatively, the reference posture data set may no longer be consistent with the CA signals collected by the IMD.

Once a calibration procedure is entered, flow moves to 604. At 604, the one or more processors instruct the patient to move to a predefined posture. For example, the predefined posture may be to stand in a vertical position and in a rest state. Alternatively, the predefined posture may be to lay horizontally in a prone or supine position. The processors may direct a user interface of a local external device to provide the instruction visually and/or audibly to the patient. Additionally or alternatively, the instruction may be provided as a predefined pattern of vibrations or electrical stimulation delivered from the IMD or otherwise.

At 606, the one or more processors collect device location information, such as from the physiologic sensor 170. As explained herein, the device location information may include X, Y and Z components that are defined as DC or low-frequency components of electrical signals produced by a 3-D accelerometer. Optionally, at 608, the processors may also collect acceleration signatures, CA signals and other information.

At 608, the one or more processors calculate reference orientation angles and a posture related impedance as discussed above in connection with FIG. 3. Additionally or alternatively, the processors may calculate position and orientation information in accordance with the operations described in the '900 patent.

At 610, the one or more processors store, in memory of the IMD, a reference posture data set that includes, among other things, the reference orientation angles, posture related impedance, and predefined posture. Optionally, at 610, the processors may also store, in the memory of the IMD, acceleration signatures, CA signals and other information with the current reference posture data set.

At 612, the one or more processors determine whether to repeat the operations of FIG. 6 in connection with the same posture and/or in connection with a new posture. When the operations are to be repeated for the same posture, flow returns to 604 where the patient is instructed to remain in the same predefined posture, while new device location information is collected, alone or in combination with additional acceleration signatures and CA signals. When the operations are to be repeated for a new posture, flow returns to 604 where the patient is instructed to move to the next predefined posture. The operations at 606, 608 and 610 are repeated in connection with the new posture.

The operations of FIG. 6 automatically update one or more reference posture data set associated with one or more posture. The operations of FIG. 6 may be repeated multiple times to build a database of reference posture data sets. The database of reference posture data sets may be utilized to define ranges of reference orientation angles and posture related impedances that may be collectively associated with a single predefined posture. For example, the standing posture may be assigned a first range of reference orientation angles θ306, φ304 (FIG. 3) and a first range of posture related impedances ΔΩ. The horizontal prone posture may be assigned a second range of reference orientation angles θ306, φ304 and a second range of posture related impedances ΔΩ. The horizontal supine posture may be assigned a third range of reference orientation angles θ306, φ304 and a third range of posture related impedances ΔΩ.

Figure 7A:
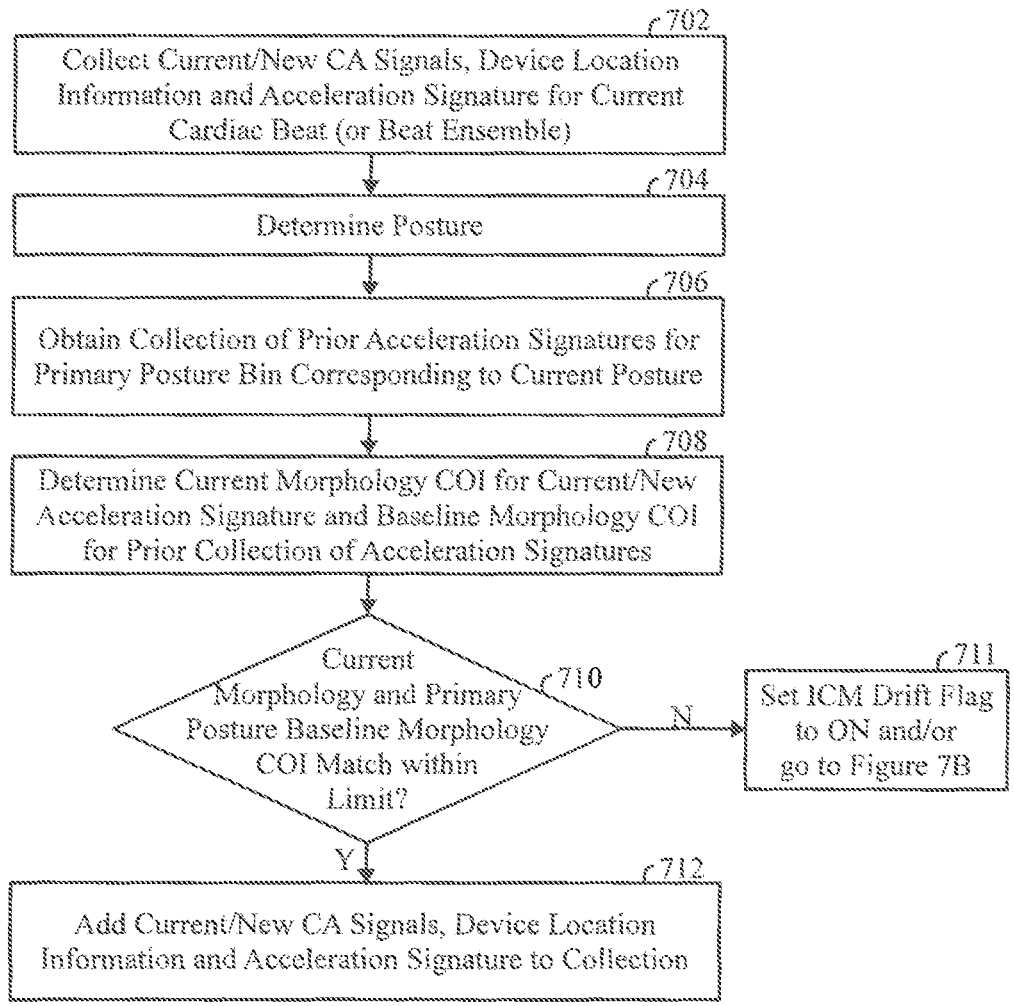
FIG. 7A illustrates a process for collecting and analyzing new CA signals in connection with posture and heart sounds in accordance with an embodiment herein.
Figure 7B:
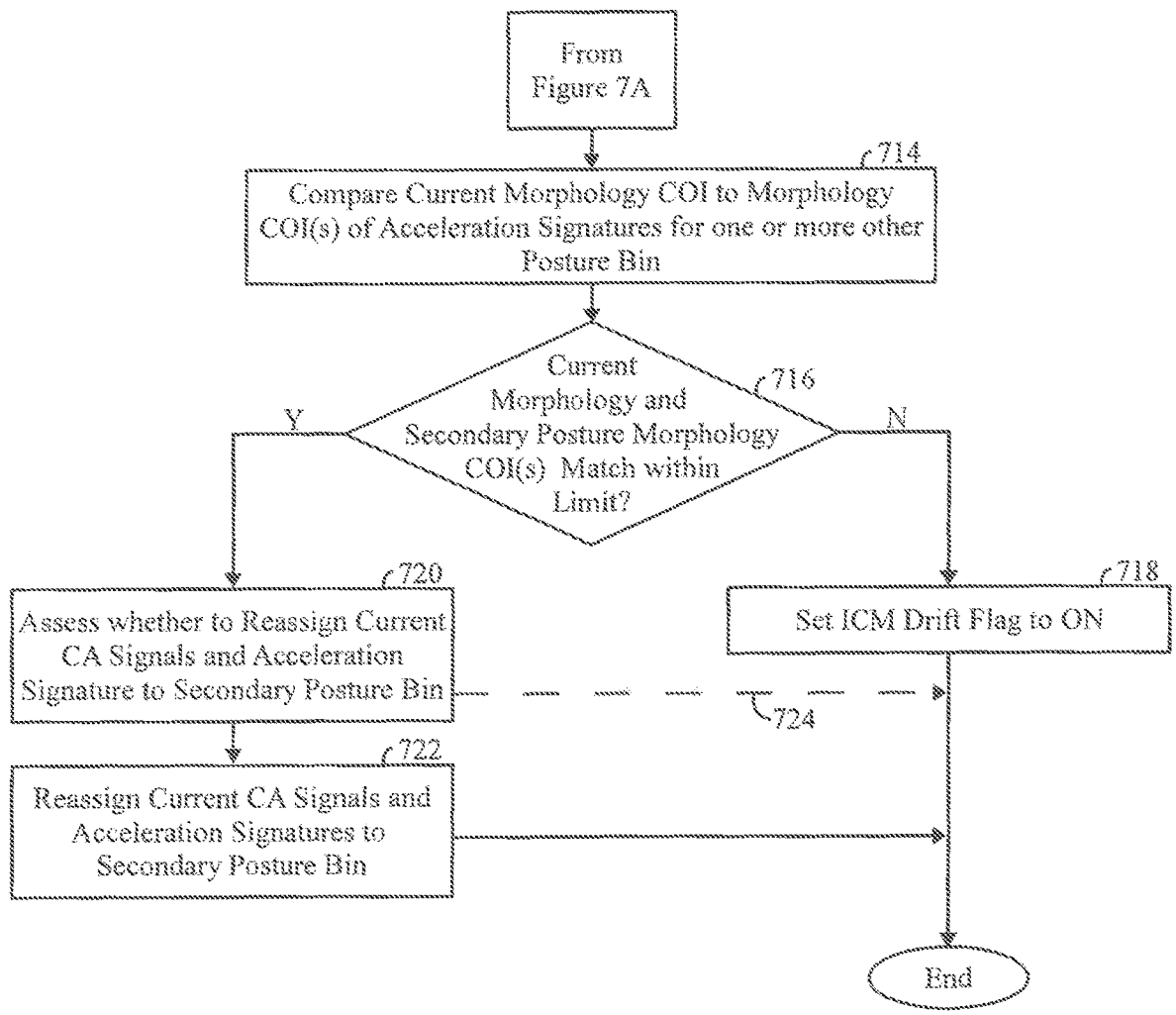
FIG. 7B illustrates a process for collecting and analyzing new CA signals in connection with posture and heart sounds in accordance with an embodiment herein.

FIGS. 7A-7B illustrate a process for collecting and analyzing new CA signals in connection with posture and heart sounds in accordance with an embodiment herein. At 702, one or more processors collect current/new CA signals, as well as device location information and an acceleration signature for a current cardiac beat. Additionally or alternatively, the processors may collect the CA signals, device location information and acceleration signature for multiple beats and combined the collected information to form an ensemble for each corresponding type of information (e.g., a CA signal ensemble, device location information ensemble and acceleration signature ensemble).

At 704, the one or more processors determine a posture of the IMD (and presumably the patient) based on the device location information. The IMD posture is designated as a primary posture that is initially utilized in connection with the operations of FIG. 7A.

At 706, the one or more processors access a posture bin that includes a collection of prior acceleration signatures that have previously been recorded and stored. The posture bin corresponds to the primary posture determined at 704 and thus the posture bin may also be referred to as a primary posture bin.

At 708, the one or more processors determine a current morphology COI for the current/new acceleration signature(s). The processors determine or obtain a baseline morphology COI for the prior collection of acceleration signatures from the primary posture bin. Optionally, the morphology COI for the collection in the primary posture bin may have been previously determined and stored, such as each time the primary posture bin is updated with new acceleration signatures.

At 710, the one or more processors compare the morphology COIs and determine whether the current morphology COI and the baseline morphology COI (for the primary posture bin) match within a predetermined COI correlation limit. When the morphology COIs match within the correlation limit, flow moves to 712. At 712, the one or more processors add the current/new CA signals, device location information and acceleration signature to the collection associated with the primary posture bin, and optionally update the baseline morphology COI.

Returning to 710, when the morphology COIs do not match within the limit, flow moves to 711. At 711, the one or more processors determined that the IMD may have drifted within the patient, such that the physical position and orientation of the IMD have changed within the subcutaneous pocket relative to the prior position and orientation at the time of implant and/or at a later calibration time. At 711, the processors set an IMD drift flag to an ON state thereby indicating that the IMD may have experienced drift. Optionally, at 711, flow moved to FIG. 7B.

Moving to FIG. 7B, at 714, the one or more processors compare the current morphology COI to the morphology COI for acceleration signatures of one or more other posture bins that differ from the primary posture bin. For convenience, the other posture bins may be designated as secondary posture bins. At 716, the one or more processors determine whether the current morphology COI and the morphology COI for the secondary posture bin match within a correlation limit. When the current and secondary morphology COIs do not match within the correlation limit, flow moves to 718. At 718, the one or more processors determined that the IMD may have drifted within the patient, such that the physical position and orientation of the IMD have changed within the subcutaneous pocket relative to the prior position and orientation at the time of implant and/or at a later calibration time. At 718, the processors set an IMD drift flag to an ON state thereby indicating that the IMD may have experienced drift.

Returning to 716, when the current morphology does not match within a correlation limit to the morphology COIs of any of the secondary posture bins, flow moves to 720. At 720, the one or more processors determine/assess whether to reassign the current/new CA signals and acceleration signature to the secondary posture bin to which the morphology COIs match. If so, at 722, the one or more processors reassign the current CA signals and acceleration signature to the secondary posture bin in the process of FIG. 7B ends. Alternatively, at 720, if it is determined that no reassignment should be performed, the operation at 722 is skipped through path 724.

Optionally, the operations of FIG. 7B may be omitted entirely and the current morphology COI only compared to the morphology COIs associated with the primary posture bin. When the comparison to secondary posture bins of FIG. 7B is omitted, optionally, at 710, flow branches directly to 718 in FIG. 7B where the one or more processors set an IMD drift flag to an ON condition.

Figure 8:
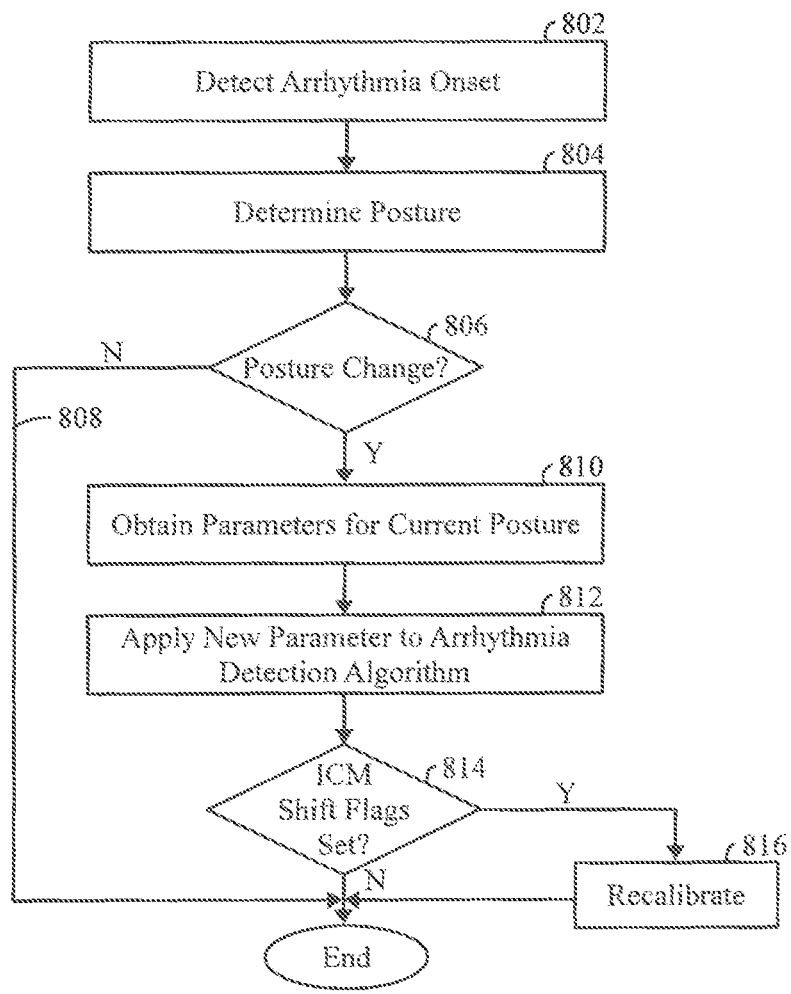
FIG. 8 illustrates a process for adjusting arrhythmia detection parameters based on posture in accordance with embodiments herein.

FIG. 8 illustrates a process for adjusting arrhythmia detection parameters based on posture in accordance with embodiments herein. At 802, the one or more processors detect onset of an arrhythmia. For example, the processors may detect onset of a bradycardia event, a pause in cardiac events, atrial fibrillation and the like. At 804, the one or more processors analyze current device location information to determine a current posture. At 806, the one or more processors determine whether a posture change has occurred from a prior posture determination. When no posture change occurs, flow moves along 808, and the arrhythmia detection algorithm continues to operate utilizing the previously set parameters. Alternatively, when a posture changes identified at 806, flow continues to 810.

At 810, the one or more processors obtain a set of arrhythmia detection parameters associated with the current posture. For example, when a current posture corresponds to a supine position, the arrhythmia detection parameters may utilize one set of thresholds, and when the current posture corresponds to a standing posture, the arrhythmia detection parameters may utilize a second set of thresholds.

At 812, the processors apply the new parameters, corresponding to the current posture, to the arrhythmia detection algorithm. Thereafter, the arrhythmia detection algorithm utilizes the new parameters in connection with analyzing subsequent CA signals. For example, the new parameters may be utilized to monitor a remaining duration of a bradycardia episode, and atrial fibrillation episode and the like.

Additionally or alternatively, the arrhythmia detection algorithm may revert back and apply the new parameter values while re-analyzing the CA signals previously utilized to detect onset of the arrhythmia (at 802). For example, the new parameters may be utilized as a confirmatory arrhythmia detection analysis wherein a collection of CA signals (e.g., a 30 second ECG strip) is reanalyzed in accordance with the operations of FIG. 8.

At 814, the one or more processors check an IMD drift flag to determine whether the IMD drift flag has been set to an ON condition. When the IMD drift flag is set to the ON condition, the processors interpret the flag to indicate that the IMD may have shifted within the subcutaneous implant pocket/region. When the IMD drift flag is set, flow moves to 816 where the processors perform the recalibration procedures described herein. Alternatively, when the IMD drift flag is unset (e.g., in an off condition), flow continues and the process of FIG. 8 ends.

Figure 9:
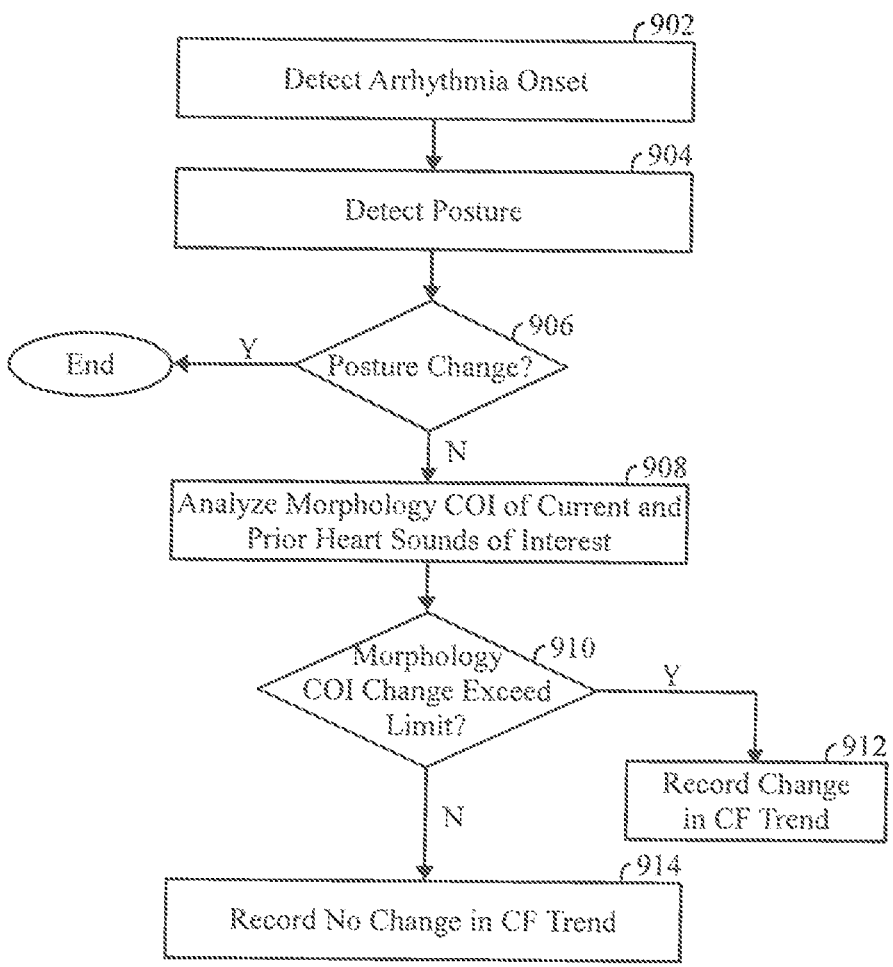
FIG. 9 illustrates a process for confirming arrhythmia detection based on changes in cardiac function in accordance with embodiments herein.

FIG. 9 illustrates a process for confirming arrhythmia detection based on changes in cardiac function in accordance with embodiments herein. At 902, the one or more processors detect onset of an arrhythmia. For example, the processors may detect onset of a bradycardia event, a pause in cardiac events, atrial fibrillation and the like. At 904, the one or more processors analyze current device location information to determine a current posture. At 906, the one or more processors determine whether a posture change has occurred from a prior posture determination. When a posture change is identified at 906, the process of FIG. 9 ends. Alternatively, when no posture change occurs, flow moves to 908.

At 908, the one or more processors analyze the morphology COI for the current and prior heart sounds of interest. The processors identify a morphology COI in one or more of the heart sounds in a current acceleration signature. The processors also identify a morphology COI in the same one or more heart sounds from prior acceleration signatures corresponding to the posture identified at 904. The processors compare the current and prior morphology COIs. At 910, the processors determine whether the current morphology COI has changed by more than a predetermined limit from the prior morphology COI. When the current morphology COI changes more than the predetermined limit, flow moves to 912. At 912, the one or more processors record a change in cardiac function trend associated with the present heart condition. Alternatively, at 910, when the current morphology COI is relatively similar to (e.g., within the limit of) the prior morphology COI, flow continues to 914. 914, the one or more processors record no change in the cardiac function trend.

It is recognized that the change in cardiac function trend may indicate a positive change in trend or a negative change in trend. For example, a change in the third heart sound S3 may indicate a change in contractility. When the change in the third heart sound S3 indicates a decreasing trend in contractility, while a patient is laying down, the condition could represent a positive indicator that a heart failure condition is improving.

Additionally or alternatively, the processors at 912 and 914 may record a confirmation or denial of an arrhythmia determination declared at 902. For example, a change in trend at 912 may correspond to and serve of the confirmation of the detection of an arrhythmia onset (determined at 902). Alternatively, when no change in cardiac function trend is indicated, the processors may also record a denial of the arrhythmia detected at 902.

CLOSING

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof)

may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A computer implemented method for detecting arrhythmias in cardiac activity, comprising:
    under control of one or more processors configured with specific executable instructions,
    obtaining cardiac activity (CA) signals, at electrodes of an implantable medical device (IMD), in connection multiple cardiac beats and in connection with different IMD orientations relative to gravitational force;
    obtaining acceleration signatures, at a sensor of the IMD, indicative of heart sounds generated during the cardiac beats;
    obtaining device location information, at the IMD, with respect to the gravitational force during the cardiac beats;
    determining when the IMD shifts within a subcutaneous implant region based on the device location information;
    grouping the acceleration signatures associated with first and second sets of cardiac beats into a corresponding one of first and second posture bins based on the device location information and based on the determination of the IMD shift; and
    identifying a difference between the acceleration signals in the first posture bin in connection with treating a heart condition.

2. The method of claim 1, further comprising treating the heart condition by at least one of: i) identifying a progression of heart failure over time; ii) confirming an arrhythmia identified by an arrhythmia detection process; iii) instructing the patient to perform a recalibration procedure or iv) delivering a therapy.

3. The method of claim 1, further comprising detecting an arrhythmia, determining whether a current patient posture has changed based on the device location information; and applying a new parameter value to an arrhythmia detection algorithm where the new parameter value is based on the current patient posture.

4. The method of claim 1, wherein the determining operation avoids comparing the acceleration signatures that are obtained when the IMD has shifted to an unknown posture with the acceleration signatures from the first and second posture bins.

5. The method of claim 1, wherein the grouping operation comprises grouping a first set of acceleration signatures and skips the grouping operation for the acceleration signatures that are obtained when the IMD has shifted in the subcutaneous implant region.

6. The method of claim 1, wherein the difference corresponds to a difference in at least one of an S1 amplitude, an S1 frequency, or a peak to peak timing between heart sounds in the acceleration signatures.

7. The method of claim 1, further comprising assigning the cardiac beats associated with a first posture to the first posture bin, and assigning the cardiac beats associated with a second posture to the second posture bin and not assigning the cardiac beats associated with an unknown posture.

8. A computer implemented method for detecting arrhythmias in cardiac activity, comprising:
    under control of one or more processors configured with specific executable instructions,
    obtaining cardiac activity (CA) signals, at electrodes of an implantable medical device (IMD), in connection multiple cardiac beats and in connection with different IMD orientations relative to gravitational force;
    obtaining acceleration signatures, at a sensor of the IMD, indicative of heart sounds generated during the cardiac beats;
    obtaining device location information, at the IMD, with respect to the gravitational force during the cardiac beats;
    grouping the acceleration signatures associated with first and second sets of cardiac beats into a corresponding one of first and second posture bins based on the device location information;
    identifying a difference between the acceleration signals in the first posture bin in connection with treating a heart condition; and
    comparing when a position of the IMD does not fall into the first and second posture bins; and based thereon declaring a IMD drift condition to be that the IMD has moved or rotated.

9. The method of claim 8, further comprising determining a morphology characteristics of interest associated with the first posture bin differs from one another by more than a correlation limit; and when the correlation limit is exceeded, the declaring operation comprising setting an IMD shift flag to an on condition.

10. The method of claim 9, wherein first and second posture bins correspond to first and second body postures, respectively, the determining operation comparing the acceleration signatures in the first posture bin to one another and comparing the acceleration signatures in the second posture bin to one another to identify a progression of heart failure over time.

11. A system, the system comprising:
    one or more processors; and
    a memory coupled to the one or more processors, wherein the memory stores program instructions, wherein the program instructions are executable by the one or more processors to:
    obtain cardiac activity (CA) signals, at electrodes of an implantable medical device (IMD), in connection multiple cardiac beats and in connection with different IMD orientations relative to gravitational force;
    obtain acceleration signatures, at a sensor of the IMD, indicative of heart sounds generated during the cardiac beats;

obtain device location information, at the IMD, with respect to the gravitational force during the cardiac beats;

determining when the IMD shifts within a subcutaneous implant region based on the device location information;

group the acceleration signatures associated with first and second sets of cardiac beats into a corresponding one of first and second posture bins based on the device location information and based on the determination of the IMD shift; and identify a difference between the acceleration signals in the first posture bin in connection with treating a heart condition.

12. The system of claim 11, wherein the one or more processors are further configured to identify at least one of differences or similarities between the acceleration signals in the second posture bin in connection with treating the heart condition; and to deliver a therapy in connection treating the heart condition.

13. The system of claim 11, wherein the one or more processors are housed within the IMD that represents one of a therapy delivery IMD and a cardiac monitoring device, the one or more processors further configured to treat the heart condition by at least one of: i) identifying a progression of heart failure over time; ii) confirming an arrhythmia identified by an arrhythmia detection process; iii) instructing the patient to perform a recalibration procedure or iv) delivering a therapy.

14. The system of claim 11, wherein the one or more processors are further configured to compare morphology characteristics of interest for acceleration signatures within the first posture bin to a correlation limit; and, based on the comparing operation, declare an IMD shift condition.

15. The system of claim 11, further comprising at least one of a remote server or a local external device housing that includes at least one of the one or more processors that are configured to perform the group and identify operations.

16. The system of claim 11, further comprising a user interface, the one or more processors configured to implement a calibration procedure comprising: providing a patient instruction through the user interface to move to a predefined posture, collect device location information while at the predefined posture, calculate reference orientation angles and store a reference posture data set comprising the device location information and reference orientation angles.

17. The system of claim 11, wherein the one or more processors are configured to group and store the acceleration signatures into the first and second posture bins for corresponding body postures and for corresponding heart rate ranges, the one or more processors configured to determine the heart condition based in part on changes in heart sounds within the acceleration signatures for a first body posture and a first heart rate range.

18. The system of claim 11, wherein the one or more processors are further configured to avoid comparing the acceleration signatures that are obtained when the IMD has shifted to an unknown posture with the acceleration signatures from the first and second posture bins.

19. The system of claim 11, wherein the one or more processors are further configured to skips the grouping operation for the acceleration signatures that are obtained when the IMD has shifted in the subcutaneous implant region.

20. The system of claim 11, wherein the one or more processors are further configured to not assign the cardiac beats associated with an unknown posture.

* * * * *